(12) United States Patent
Remde et al.

(10) Patent No.: US 8,715,268 B2
(45) Date of Patent: May 6, 2014

(54) ADMINISTRATION DEVICE HAVING A BOLUS ADMINISTRATION PROFILE CONTROLLER

(75) Inventors: Axel Remde, Luetzelflueh (CH); Lucas Kalt, Münchenbuchsee (CH)

(73) Assignee: Roche Diagnostics International AG, Rotkreuz (CH)

( * ) Notice: Subject to any disclaimer, the term of this patent is extended or adjusted under 35 U.S.C. 154(b) by 211 days.

(21) Appl. No.: 12/858,480

(22) Filed: Aug. 18, 2010

(65) Prior Publication Data

US 2011/0202040 A1    Aug. 18, 2011

Related U.S. Application Data

(63) Continuation of application No. PCT/EP2009/001125, filed on Feb. 18, 2009.

(30) Foreign Application Priority Data

Feb. 21, 2008  (EP) .................................. 08003164

(51) Int. Cl.
*A61K 9/22* (2006.01)
*A61M 31/00* (2006.01)

(52) U.S. Cl.
USPC .......................................... 604/890.1; 604/67

(58) Field of Classification Search
USPC .......... 604/890.1, 891.1, 30, 65–67, 503–505
See application file for complete search history.

(56) References Cited

U.S. PATENT DOCUMENTS

| | | | |
|---|---|---|---|
| 4,562,751 A | 1/1986 | Nason et al. | |
| 6,248,093 B1 | 6/2001 | Moberg | |
| 6,736,796 B2 | 5/2004 | Shekalim | |
| 6,878,132 B2 | 4/2005 | Kipfer | |
| 2003/0114836 A1 | 6/2003 | Estes et al. | |
| 2003/0160683 A1* | 8/2003 | Blomquist | ............... 340/309.16 |
| 2005/0171513 A1* | 8/2005 | Mann et al. | ................. 604/890.1 |
| 2005/0238507 A1 | 10/2005 | Dilanni et al. | |

FOREIGN PATENT DOCUMENTS

| | | |
|---|---|---|
| EP | 0099144 | 6/1983 |
| EP | 1 124 600 B1 | 10/1999 |
| EP | 1 338 295 A1 | 8/2003 |
| WO | 98/47552 | 4/1998 |
| WO | 00/25844 | 5/2000 |
| WO | 2006/089965 A1 | 8/2006 |
| WO | 2006/124716 A2 | 11/2006 |
| WO | 2007/056592 A2 | 5/2007 |

OTHER PUBLICATIONS

PCT International Search Report for Application No. PCT/EP2009/001125 f. Feb. 18, 2009, 7 pages.

* cited by examiner

*Primary Examiner* — Bhisma Mehta
*Assistant Examiner* — Bradley Osinski
(74) *Attorney, Agent, or Firm* — Dinsmore & Shohl LLP

(57) ABSTRACT

According to one embodiment, an administration device for subcutaneous administration of a liquid drug over an extended period of time is provided. The administration device may include an administration unit, a housing, and a controller unit. The administration unit may include a drug reservoir and a pump unit. The housing may include the administration unit and may be adapted to be carried by a patient over an extend period of time. The controller unit may include a bolus administration profile controller. The bolus administration profile controller receives a bolus volume of a bolus to be administered and determines based, at least in part, on the bolus volume a bolus administration profile such that a depot volume of a depot is limited.

22 Claims, 9 Drawing Sheets

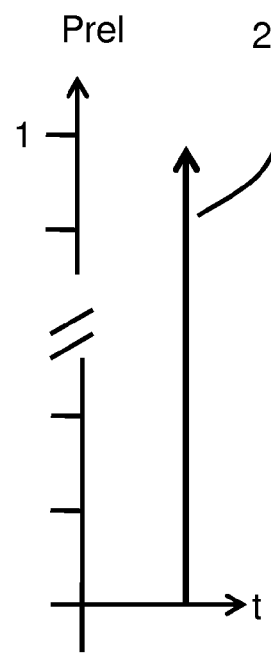
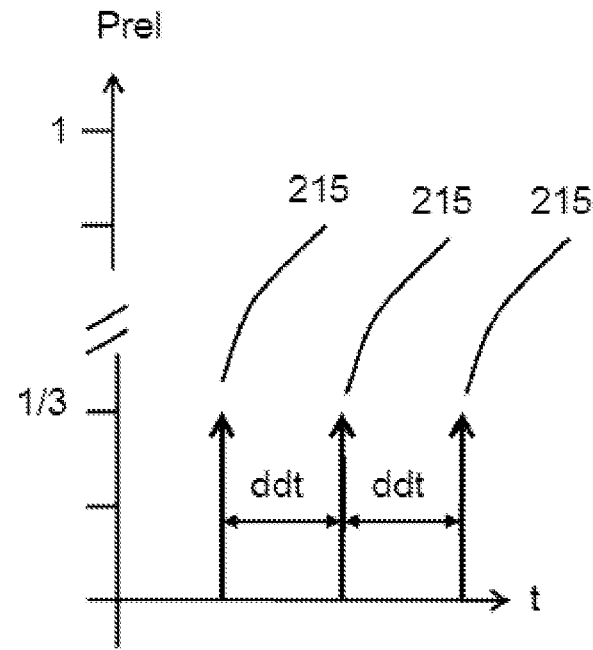
Figure 1a          Figure 1b
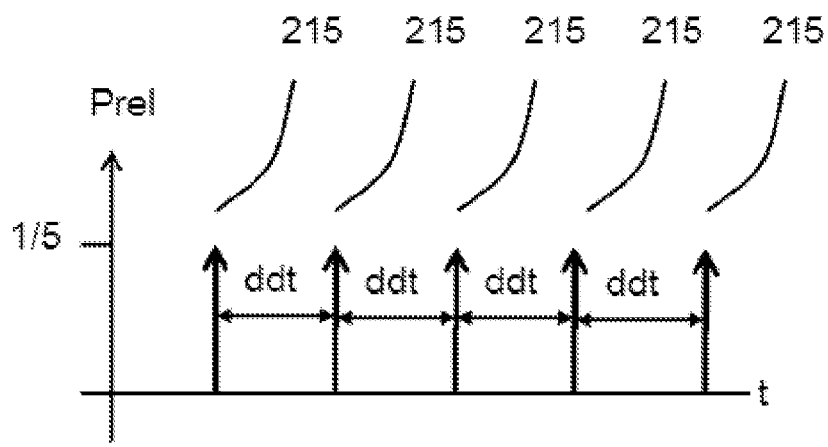
Figure 1c

ADMINISTRATION DEVICE HAVING A BOLUS ADMINISTRATION PROFILE CONTROLLER

CROSS REFERENCE TO RELATED APPLICATIONS

This application is a continuation of International Application No. PCT/EP2009/001125 filed Feb. 18, 2009 which claims priority to European Patent Application No. EP08003164.4 filed on Feb. 21, 2008, both of which are incorporated by reference herein.

TECHNICAL FIELD

The present disclosure is related to administration devices for the subcutaneous administration of a liquid drug over an extended period of time and to methods for controlling the subcutaneous administration of a bolus of a liquid drug by administration devices. Further embodiments are related to administration devices for diabetes therapy using Continuous Subcutaneous Insulin Infusion (CSII) and to methods for the administration of insulin boli.

BACKGROUND

Continuous Subcutaneous Insulin Infusion (CSII) may be the basis for therapy of insulin-dependent diabetes mellitus. In some examples of this therapy, a diabetic patient carries a miniaturized infusion pump quasi-continuously throughout night and day and possibly concealed from view. The infusion pump administers insulin via a cannula, the cannula being, e.g., made from medical-grade stainless steel or Teflon, into the subcutaneous fat tissue. The cannula may also be an arrangement of several cannulas such as a micro needle array, or the like.

According to a first administration regime, the insulin pump administers insulin in a continuous or quasi-continuous way as defined by patient-specific and time-of-day dependent basal profile in order to cover the patient's basal (i.e., meal-independent) insulin need. According to a second administration regime, the pump is adapted to administer comparatively large insulin boli on demand for covering the intake of food, namely carbohydrates, and to correct for undesirably high blood glucose values. Infusion devices which are adapted fort the CSII therapy of diabetes mellitus are disclosed, among others, in U.S. Pat. No. 6,878,132, which is incorporated by reference herein.

While quasi-continuous basal administration typically comprises small drug volumes, bolus volumes are considerably larger in some cases, often resulting in bad and delayed drug absorption and high internal tissue pressure, potentially resulting in tissue damage. In some cases, the insulin may, in total or in part, flow back from the cannula tip along the outer cannula surface and leave the body, resulting in a lack of drug administration.

SUMMARY

According to one embodiment, an administration device for subcutaneous administration of a liquid drug to tissue of a patient over an extended period of time is provided. The administration device may include an administration unit, a housing, and a controller unit. The administration unit comprises a drug reservoir and a pump unit. The housing comprises the administration unit and may be adapted to be carried by a patient over an extend period of time. The controller unit comprising a bolus administration profile controller. The bolus administration profile controller receives a bolus volume of a bolus to be administered and determines based, at least in part, on the received bolus volume a bolus administration profile such that a depot volume of a depot is limited, wherein the depot is a subcutaneous drug depot that is present during and shortly after the administration until the drug is absorbed by the tissue.

In another embodiment, a method for controlling a pump unit of an administration device is provided. The administration device is adapted for the subcutaneous administration of a liquid drug to tissue of a patient over an extended period of time. The method may include: providing a bolus volume of a bolus to be administered; determining, with a bolus administration profile controller, a bolus administration profile of the bolus to be administered, at least in part, based on the provided bolus volume, wherein the depot volume of a depot is limited, and wherein the depot is a subcutaneous drug depot that is present during and shortly after the administration until the drug is absorbed by the tissue; and controlling the pump unit to administer the bolus according to the bolus administration profile determined by the bolus administration profile controller.

These and additional features provided by the embodiments described herein will be more fully understood in view of the following detailed description, in conjunction with the drawings.

BRIEF DESCRIPTION OF THE DRAWINGS

The embodiments set forth in the drawings are illustrative and exemplary in nature and not intended to limit the subject matter defined by the claims. The following detailed description of the illustrative embodiments can be understood when read in conjunction with the following drawings, where like structure is indicated with like reference numerals and in which:

FIG. 1a through FIG. 1d depict alternative bolus administration profiles according to one or more of the embodiments shown and described herein;

DETAILED DESCRIPTION

As used herein with the various illustrated embodiments described below, the following terms related to subcutaneous drug administration include, but are not limited to, the following meanings.

The term 'absorption' refers to the uptake of the administered drug by the subcutaneous tissue. The term 'steady absorption' is used for an absorption while performing the drug administration while the term 'delayed absorption' is used for an delayed absorption from a depot as defined below. Absorption is generally dependent on the flow during administration and/or the average administration rate over an extended period of time, dependent on the administration regime. It is further dependent on factors such as the length and design of the administration cannula, the patient's tissue properties, and so on.

The term 'depot' refers to a drug which is temporarily stored in the subcutaneous tissue prior to its delayed absorption by the tissue. In this context, a depot may be considered as a locally concentrated drug cloud in the tissue around the cannula.

The term 'flow' refers to the momentary flow, i.e. the drug volume which is administered per time, as a function of time. For example, flow may be measured by a flow sensor as a function of time t at the cannula. Flow is generally measured in volume per time, e.g., International Units per second, [IU/sec].

The term 'administration rate' refers to a general measure for the drug volume which is administered per time and may be either an actual flow or an average flow over a given period of time. Generally, the term 'rate' refers to a volume per time.

The term 'pulse' refers to Dirac administration of a defined drug volume over a negligibly short duration of time. It must be understood, however, that the modeling of individual drug administrations as Dirac pulses is helpful for the mathematical and graphical representation in many cases, while the actual flow is generally complex depending on the design and the control of the administration device.

The term 'continuous' is used in the context of drug administration if the flow is generally non-zero during the administration. Typically, but not necessarily, the flow is substantially constant during the administration. In contrast, the term 'pulsed' is used if the administration comprises periods with the flow being substantially zero and periods with the flow being non-zero. It should be noted that an administration device may technically be operated in a pulsed way, using, e.g., a drive mechanism which is driven a stepper motor, while the flow may be continuous due to fluid inertia and system elasticity.

Figure 1D:
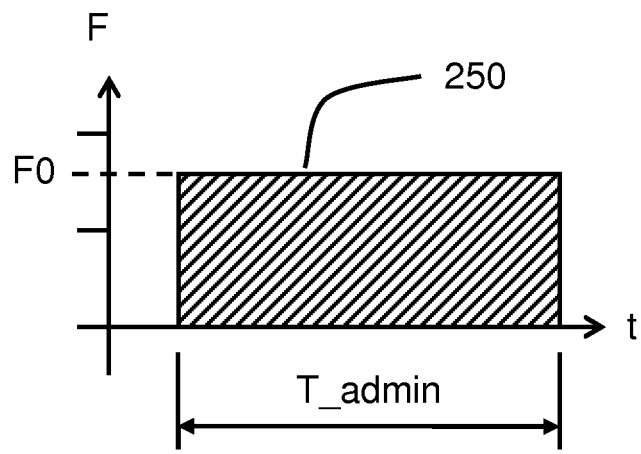

Referring to FIG. 1a, the term 'bolus administration profile' refers to the distribution of a bolus volume to be administered over time t. The relative pulse volume P_rel is the pulse volume of a pulse divided by the bolus volume. FIG. 1a graphically depicts the administration of a bolus, the bolus having a bolus volume, according to a bolus administration profile with the total bolus volume being administered as a single immediate bolus pulse 210. FIG. 1b graphically depicts the administration of a bolus having the same bolus volume according to a second bolus administration profile with the bolus volume being administered as three extended bolus pulses 215, each of the three extended bolus pulses 215 having a bolus pulse volume of one third of the bolus volume, the bolus pulse intervals ddt between the extended bolus pulses 215 being equal. FIG. 1c graphically depicts the administration of a bolus having the same bolus volume according to a third bolus administration profile with the bolus volume being administered as five extended bolus pulses 215, each of the five extended bolus pulses having a bolus pulse volume of one fifth of the bolus volume, the bolus pulse intervals ddt between the extended bolus pulses 215 being equal. FIG. 1d graphically depicts the administration of a bolus having the same bolus volume according to a fourth bolus administration profile. The bolus volume is administered continuously with a substantially constant flow F0 over an administration time T_admin, such that the integral of the flow F over time t, i.e., the area F0*T_admin of rectangle 250, equals the bolus volume. Further bolus administration profiles may be obtained by keeping the integral of the flow F over the time t equal the bolus volume such as, for example, by performing the administration continuously with an alternative substantially constant flow, the alternative substantially constant flow being different from the substantially constant flow F0, or by varying the flow F over time t according to a given function.

The term 'bolus administration profile' may be used in the context of a bolus in total but may also be used for at least two sub boli. The at least two sub boli having corresponding sub bolus volumes summing up to the bolus volume. In this case, the term 'bolus administration sub profile' may be used for clarity reasons for the corresponding bolus administration profiles. It has to be understood, however, that the distribution of a bolus volume over time t may generally be described by one more complex bolus administration profiles instead.

The terms 'immediate bolus' and 'immediate bolus administration profile' refer to a bolus which is administered within a short administration time after receiving a bolus administration command. The administration time is substantially negligible, as compared to the pharmaceutical effect resulting from the drug after administration. The actual administration time for an immediate bolus may range from a fraction of a second to many seconds, e.g. 30 seconds, dependent on factors such as the design of the administration device and the bolus volume of the immediate bolus.

The terms 'extended bolus' and 'extended bolus administration profile' refer to a bolus which is administered over a controlled extended period of time, the extended period of time being generally large as compared to the administration time of an immediate bolus. An extended bolus may be administered continuously or may be administered as a series of extended bolus pulses which make up the extended bolus. The administration of an extended bolus may be started immediately after receiving a bolus administration command or may be started after a delay.

Figure 2A:
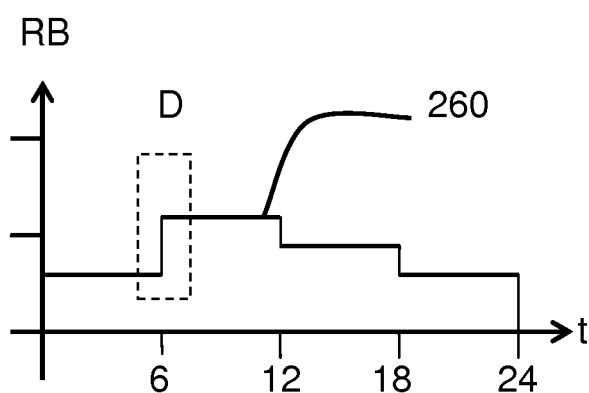
FIG. 2a depicts a basal profile over the time of day according to one or more of the embodiments shown and described herein.

Referring to FIG. 2a, the term 'basal profile' refers to the basal administration rate RB over time t. For example, curve 260 is graphically depicted in FIG. 2a and corresponds to a basal profile for drug (e.g., insulin) administration over the time of day in the framework of CSII. The basal profile is generally patient-dependent and is defined by the basal administration rate RB over the time of day. For the example, the basal administration rate RB depicted in FIG. 2a is varied in four blocks over the day with the basal administration rate RB being identical within each block. The basal administration rate is may be measured in International Units per hour, [IU/h].

Figure 2B:
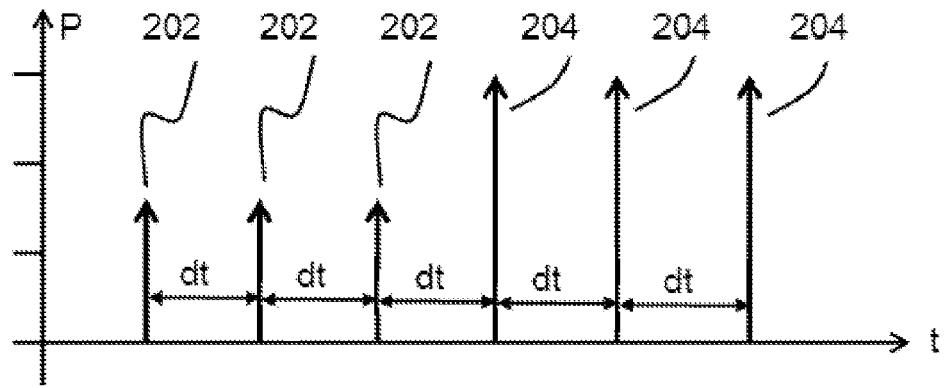
FIG. 2b depicts a detail view of a basal administration profile for basal administration according to FIG. 2a according to one or more of the embodiments shown and described herein.

Referring to FIG. 2b, the term 'basal administration profile' refers to the actual flow resulting form basal administration over time t. According to a first basal administration profile, basal administration is performed continuously with the flow caused by basal administration being substantially equal to the basal administration rate RB at any moment of time t. According to another basal administration profile, basal administration is pulsed. FIG. 2b graphically depicts a pulsed basal administration profile where basal pulses 202, 204 are administered in equal basal pulse intervals dt, with the basal pulse volume of the basal pulses 202, 204 being an equal portion of the basal drug volume which is administered in one hour of a day. FIG. 2b graphically depicts an enlarged view of detail D in FIG. 2a. The basal pulse interval dt may, for example, be 3 minutes such that each basal pulse 202, 204 administers ½0th of the basal drug volume which is administered in one hour of a day.

The embodiments described herein relate to administration devices for the subcutaneous administration of a liquid drug over an extended period of time which may improve absorption and reduce flow back of administered drug doses. For example, boli may be administered as described herein without requiring a patient to consider drug absorption.

The embodiments described herein relate to methods for controlling a pump unit of an administration device which may improve absorption and reduce flow back of administered drug doses such as, for example, boli. Additionally, it is noted that the devices and methods described herein may be utilized in the framework of diabetes therapy by CSII, and in the framework of different therapies such as pain therapy.

The embodiments described herein may be further understood with reference to an empirical and semi-quantitative absorption model. It is noted that the model is provided for clarity, and the embodiments described herein should not be limited to any theoretical model. In the following, the model is relates to the administration of a bolus having the bolus volume, but also holds true, mutatis mutandis, for subcutaneous administration in a more general context such as, for example, combined bolus and basal administration. Steady absorption by the tissue surrounding the cannula tip is only possible for a flow not exceeding a maximum steady absorption rate, the maximum steady absorption rate is typically in a range of some IU/min in the framework of CSII.

For an actual flow exceeding this maximum steady absorption rate, the actual absorption rate is given by $$R\_absorption = \begin{cases} F & \text{if } F \leq R\_max \\ R\_max & \text{if } F > R\_max \end{cases} \quad (1)$$

, where R_absorption is the actual absorption rate, F is the actual flow, and R_max is the maximum steady absorption rate. When the actual flow exceeds the maximum steady absorption rate, the administered drug is not fully and immediately absorbed by steady absorption, but is partly stored in a depot and is subsequently delayed from the depot. Instead of the bolus volume, only a steady absorption bolus volume is absorbed by the tissue over the administration time. The steady absorption bolus volume is given by $$B\_steady = R\_max \cdot T\_admin, \quad (2)$$

where B_steady is the steady absorption bolus volume, R_max is the maximum steady absorption rate, and T_admin is the administration time. Under the assumptions that the term "F−R_max" is non-negative and that the depot is empty at the beginning of the administration, the resulting depot volume of the bolus while performing the administration is given as a function of time by $$B\_depot(t1) = \int_0^{t1} [F(\tau) - R\_max] d\tau, \quad (3a)$$

where B_depot is the resulting depot volume, F is the actual flow, R_max is the maximum steady absorption rate, T_admin is the administration time and t1 runs form zero at the beginning of the administration to the administration time.

If the depot is not empty at the beginning of the administration but contains some initial depot volume, resulting, e.g., from a previous administration, the depot volume is given by $$B\_depot(t1) = \int_0^{t1} [F(\tau) - R\_max] d\tau + B0\_depot, \quad (3b)$$

where B_depot is the resulting depot volume, F is the actual flow, R_max is the maximum steady absorption rate, T_admin is the administration time, t1 runs form zero at the beginning of the administration to the administration time, and B0_depot is initial depot volume.

The drug stored in the depot is subsequently absorbed by the tissue from the depot after a delay. For practical reasons, the delayed absorption rate is assumed to be constant and substantially equivalent to the maximum steady absorption rate, resulting in the depot volume that decreases according to a linear function. The linear function is given by $$B\_depot(t1) = B\_depot(0) - R\_max \cdot t1, \quad (4)$$

where B_depot(t1) is the resulting depot volume at t1, B_depot(0) is the depot volume for t1=0, R_max is the maximum steady absorption rate, and t1 runs from zero, i.e., starts at the end of the administration. The absorption rate, however, may also be different from the maximum steady absorption rate and/or may not be constant.

Establishing a depot results in a temporarily and local tissue pressure increase, the increased tissue pressure leading to mechanical stress which, in extreme cases, may cause local trauma and/or damage of the tissue.

If the depot volume exceeds a maximum depot volume, a drug may flow back along the outer surface of the cannula and out of the tissue. The maximum depot volume depends on several factors such as the length and design of the administration cannula, and the patient's tissue properties. It is typically in the range of about 5.0 IU to about 10.0 IU in the framework of CSII.

US Pat. Pub. Nos. US 2003/0114838 A1 and US 2003/0160683 A1, which are incorporated by reference herein, each disclose administration devices offering a variety of bolus administration profiles from which a patient or operator may manually select in order to adjust the bolus administration in dependence of the food absorption characteristics. WO 2006/124716 A2, which is incorporated by reference herein, discloses a system for automatic control of blood glucose comprising a continuous glucose sensor and an administration device, wherein a closed-loop control algorithm is employed to control the blood glucose level with a minimum insulin accumulation in the subcutaneous tissue. WO 2006/089965 A1, which is incorporated by reference herein, discloses a device and a method for providing a change in a drug delivery rate wherein dedicated administration profiles are temporarily employed to quickly fill or empty a subcutaneous depot.

Figure 3:
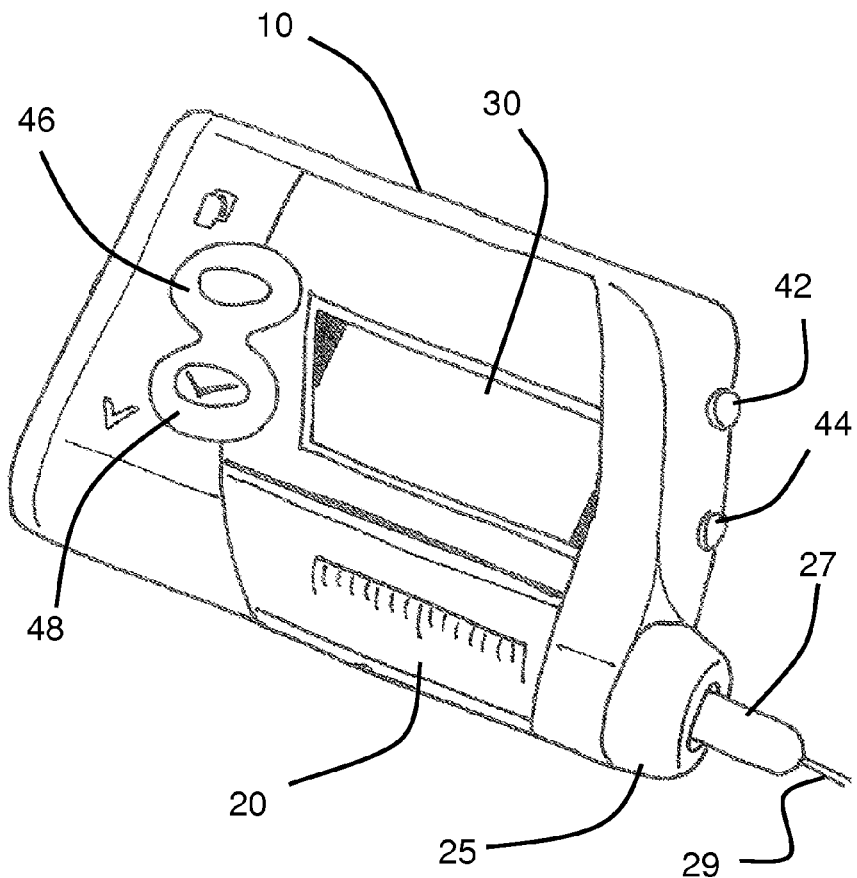
FIG. 3 schematically depicts an administration device according to one or more of the embodiments shown and described herein.
Figure 4:
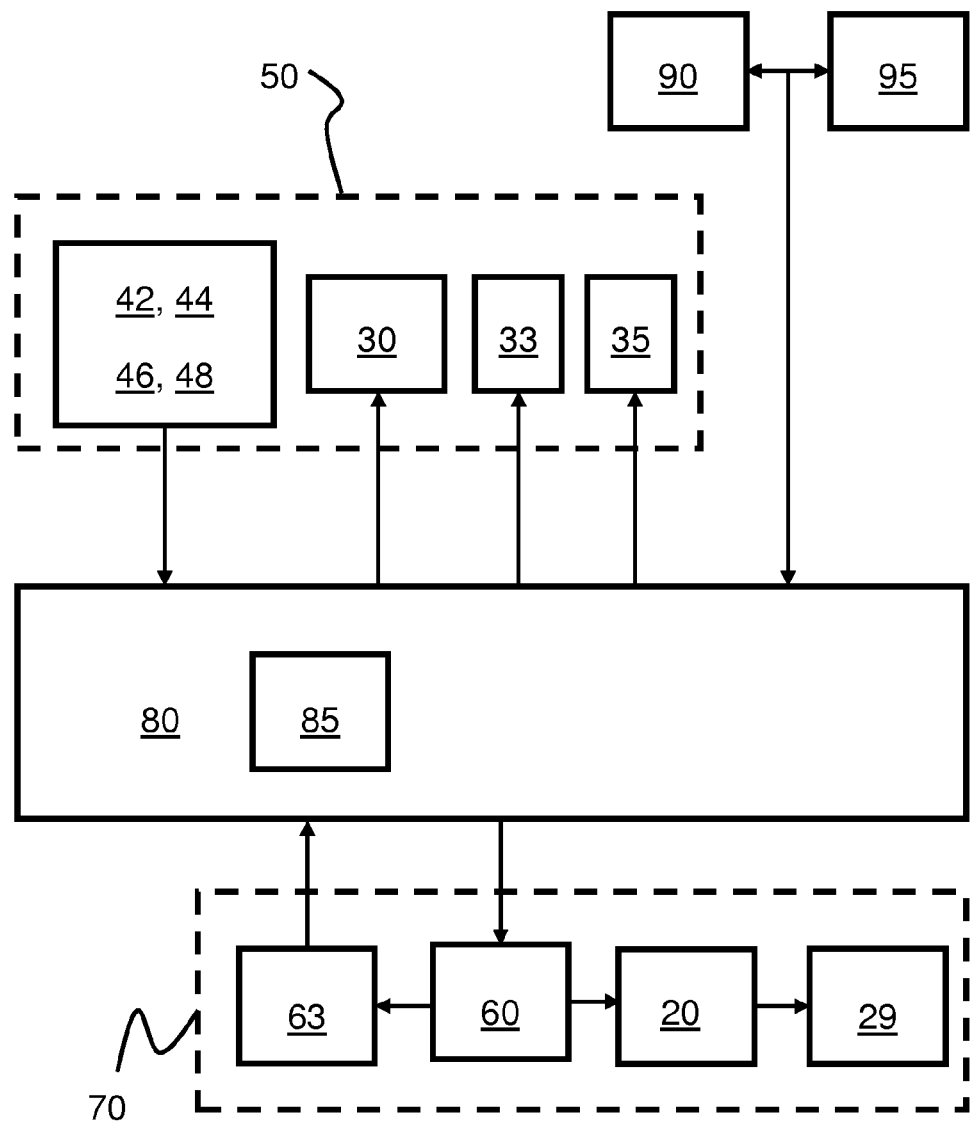
FIG. 4 schematically depicts an internal functional structure of the administration device shown in FIG. 3 according to one or more of the embodiments shown and described herein.

Referring collectively to FIGS. 3 and 4, an administration device for the subcutaneous administration of a liquid drug over an extended period of time according to embodiments of the present disclosure may include an administration unit 70, a housing 10, a controller unit 80 and a bolus administration profile controller 85. The administration unit 70 includes a drug reservoir 20 and a pump unit 60. The housing 10 includes the administration unit 70, and is adapted to be carried by a patient over an extend period of time. The controller unit 80 includes a bolus administration profile controller 85. The bolus administration profile controller 85 is adapted to receive a bolus volume of a bolus to be administered and to determine based, at least in part, on the bolus volume a bolus administration profile such that the depot volume of a depot is limited.

In embodiments described herein, for example, a bolus administration profile controller, the terms 'limit' and 'limiting' may refer to limiting the depot volume of a depot such that the depot volume does not exceed a threshold value and/or to lowering a depot volume of a depot as compared to a depot volume which may be stored in a depot without the bolus administration profile controller.

The housing may comprise the controller unit and the administration unit. Alternatively, the controller unit may be, at least in part, separate from the housing comprising the administration unit. The controller unit may be adapted to communicate with the administration unit via wired interface means such as an electrical connector or wireless interface means such as an infrared or Radio Frequency (RF) data interface.

The controller unit may be realized in general ways and may be designed using different kinds of architectures. The controller unit may comprise elements known to the those skilled in the art such as, for example, microcontrollers, Application Specific Integrated Circuits (ASICS), program memory and data memory, clock circuits, power circuits, supervision circuits, and the like.

In some embodiments, the administration device further comprises a power supply such as, for example, a one-way battery, a rechargeable battery, a capacitor, or the like.

In further embodiments, the pump unit comprises a spindle drive and a rotary motor such as, for example, a DC motor, a brushless DC motor, a stepper motor or an electromagnetic intermittent motion device. The drug reservoir comprises a barrel and a piston, the piston being controllably displaced within the barrel by spindle drive in order to perform drug administration. In alternative embodiments, the pump unit may be realized according to an alternative pump design known in the art, such as a micro membrane pump or a peristaltic pump and/or the drug reservoir may be a pouch, a bag, or the like. Embodiments of the administration unit are disclosed, among others, in EP0991440, U.S. Pat. No. 6,248,093, US Pat. No. 2005/0238507, or U.S. Pat. No. 6,736,796, which are incorporated by reference herein.

The bolus volume may be received by a user interface via a wired or wireless interface as described in detail below in the context of embodiments of the present disclosure.

In some embodiments, it is desirable to shorten the administration time while preventing flow back and limiting the mechanical stress exerted onto the tissue. Thus, determining a bolus administration profile for a given bolus amount may be formulated as optimization problem. The bolus administration is theoretically performed as given by the formulas, independent of the bolus amount, $$B\_depot \leq BT\_depot \text{ and} \quad (I)$$

$$T\_admin \to 0, \quad (II)$$

where B_depot is the depot volume, BT_depot is the depot volume threshold, and T_admin is the administration time.

Thus, a determination of a bolus administration profile for a given bolus volume may be formulated as minimization problem for the administration time under a boundary condition for the depot volume. For a given bolus volume the bolus administration profile controller according to the embodiments described herein determines an appropriate distribution of the administration over time. In one embodiment, the bolus administration profile controller is adapted to select a bolus administration profile from a given set of bolus administration profiles and to compute one or multiple parameters of the bolus administration profile, at least in part, in dependence of the bolus volume as is described in more detail below.

The embodiments described herein may be based on the absorption model given above and/or simplifications of this absorption model in order to determine parameters and threshold values related to bolus administration. However, other absorption models such as, for example, a two-compartment model or a three-compartment model as known in the art, may be employed alone or in combination with the absorption model described herein. The absorption models may, e.g., be based on corresponding equations and/or look-up tables. The absorption models may be implemented as code in the controller unit. Furthermore, the parameters used in the embodiments described herein may be determined empirically, based, e.g., on the experience of a healthcare professional.

In one embodiment, for a given bolus volume the bolus administration profile controller determines an appropriate distribution of the administration over time. In some embodiments, the bolus administration profile controller is adapted to determine the bolus administration profile by selecting a bolus administration profile from a given set of bolus administration profiles and computing one or multiple parameters for the selected bolus administration profile based, at least in part, on the bolus volume. The bolus administration profiles may comprise an immediate bolus administration profile, an extended bolus administration and/or a combination thereof. Other types of bolus administration profiles may be also be provided additionally or alternatively.

In some embodiments, approximations and assumptions may be used which result in approximately satisfying formula (I) and/or formula (II). For example, the bolus depot amount may be limited such that the formula (I) is strictly fulfilled only if the bolus amount does not exceed a threshold value and/or the administration time may not be the smallest possible administration time for which the boundary condition is met but may result from a compromise which takes into account further aspects such as implementation complexity.

In further embodiments, the bolus administration profile controller 85 is adapted to determine the bolus administration profile such that the depot volume of a depot does not exceed a depot volume threshold. The bolus administration profile may be controlled such that the depot volume is limited to a depot volume threshold as the maximum depot volume, which is given by $$B\_depot(t) \leq BT\_depot, \quad (5)$$

where B_depot is the depot volume and BT_depot is the depot volume threshold.

In embodiments where the administration unit is adapted for substantially continuous administration of a bolus with controllable flow, the motor speed may be directly controlled. For example, the flow may be based on a spindle expressing drug from a cartridge where, the spindle is driven by a speed controlled motor, Specifically, the administration time for a given bolus volume may be controlled to meet the condition given by equation (5), with the bolus depot volume being computed, e.g., by equation (3a). The flow may be controlled to be substantially constant and controlled such that the depot is filled up to the subcutaneous bolus volume threshold while performing the administration.

In embodiments where the administration device is adapted for the administration of bolus pulses with substantially constant bolus pulse intervals between consecutive bolus pulses and a controllable bolus pulse volume per pulse, equation (3b) may be utilized to compute the bolus depot volume in order to meet the condition given by equation (5). Specifically, the single bolus pulses may be evaluated as separated bolus administrations, with the integral in equation (3b) being equivalent to a bolus pulse volume. Further, the steady absorption may be neglected while administering the pulses and the delayed absorption following the administration of each bolus pulse may be considered alone.

Pulsed administration may performed by administration devices comprising a pump unit with a motor driven spindle drive, the motor being controlled to start and stop rather than being speed controlled. If, for example, the bolus pulse interval is sufficiently long for fully absorbing the pulse volume of a bolus pulse, the initial depot volume is zero for each pulse. The bolus pulse volume may be controlled to be substantially equal the depot volume threshold. Alternatively, the current depot volume, when administering a bolus pulse, may be considered an initial depot volume for the administration of each bolus pulse according to, for example, equation (4). This administration may result in the bolus pulse volume being smaller than the depot volume threshold.

In embodiments where the administration device is adapted for the administration of bolus pulses, the condition of equation (5) may be met in a similar way by controlling the bolus pulse interval. Specifically, the bolus pulses may have a fixed bolus pulse volume and a controllable bolus pulse interval between consecutive bolus pulses. For example, the administration device may comprise a solenoid-actuated spindle drive such as, for example, as is disclosed in U.S. Pat. No. 4,562,751, which is incorporated by reference herein.

In some embodiments involving a depot volume threshold, the depot volume threshold is defined by a maximum depot volume that is the maximum depot volume that may be stored in a depot.

In other embodiments, the depot volume threshold is smaller than the maximum depot volume in order to reduce the physical stress which is exerted onto the tissue.

In further embodiments, the bolus administration profile controller is adapted to determine the bolus administration profile such that the bolus administration profile comprises an immediate bolus administration profile corresponding to an immediate bolus having an immediate bolus volume.

The immediate bolus may be administered according to different bolus administration profiles, e.g. with a substantially continuous flow, as a single bolus pulse or as a series of bolus pulses.

In embodiments involving an immediate bolus, the bolus administration profile controller may be adapted to determine the immediate bolus volume such that the immediate bolus volume does not exceed a bolus volume threshold. The bolus volume threshold may, e.g., be computed based on a given depot volume threshold using the absorption model, as described herein.

The bolus volume threshold may be defined such that the depot volume of a depot does not exceed a maximum depot volume. Alternatively, the depot volume threshold may be defined to be smaller than the maximum depot volume, and to be a given fraction of the maximum depot volume in order to reduce the physical stress which is exerted onto the tissue.

The fraction may, for example, be in the range from about 0.5 to about 0.8.

In the embodiments described herein, the bolus administration profile controller 85 may be adapted to determine the bolus administration profile such that the bolus administration profile comprises an extended bolus administration profile corresponding to an extended bolus having an extended bolus volume.

The extended bolus may be administered over an extended period of time. The extended period of time may be a fixed time of, e.g., about 15 minutes or about 30 minutes. The extended period of time may also be adjusted, e.g., based on the extended bolus volume with the extended period of time increasing with the extended bolus volume. For example, a list comprising extended periods of time may be provided and the extended period of time for administering the extended bolus may be determined to be the smallest value from this list for which the limitation criteria for the depot volume are met.

In some embodiments involving an extended bolus, the bolus administration profile controller is adapted to determine the extended bolus as a series of extended bolus pulses.

The extended bolus pulses may be administered over the extended period of time with equal bolus pulse intervals between the administration of the individual extended bolus pulses.

In embodiments where the administration device is adapted for the administration of bolus pulses with controllable bolus pulse volume and equal bolus pulse interval, computation of the extended bolus pulse volume may be based: on the extended bolus volume, the extended period of time and the bolus pulse interval. In embodiments where the administration device is adapted for the administration of bolus pulses having a fixed bolus pulse volume and a controllable bolus pulse interval, the bolus pulse interval may be computed based on the extended bolus volume, the bolus pulse volume and the extended period of time.

In embodiments involving the administration of an extended bolus as a series of extended bolus pulses, the bolus administration profile controller may be adapted to determine the bolus administration profile such that the bolus pulse volume of the extended bolus pulses does not exceed a bolus pulse volume threshold. The bolus pulse volume threshold may, e.g., be computed based on a given depot volume threshold using the absorption model, as described herein.

The bolus pulse volume threshold may be defined such that the depot volume of a depot does not exceed a maximum depot volume. Alternatively, the depot volume threshold may be defined to be smaller than the maximum depot volume, and to be a given fraction of the maximum depot volume in order to reduce the physical stress which is exerted onto the tissue. The fraction may be, for example, in the range from about 0.5 to about 0.8.

In one embodiment, when the bolus pulse interval between two consecutive extended bolus pulses is about 6 minutes, for example, an administration unit comprising a motor driven spindle drive is used for the administration and the drug is administered via a subcutaneous cannula, the bolus pulse volume threshold may be set to about 3.0 IU, for example. Such settings correspond to an assumption that 3.0 IU of subcutaneously administered drug can be delayed absorbed within a period of about 3 minutes.

In further embodiments, the bolus administration profile controller is adapted to determine at least a first bolus administration sub profile and a second bolus administration sub profile, and to determine at least a first bolus sub volume and a second bolus sub volume. The at least two bolus administration sub profiles, in combination, form the bolus administration profile and the at least two bolus sub volumes sum up to the bolus volume. With a first bolus administration sub profile corresponding to an immediate bolus having an immediate bolus volume B_immediate and a second bolus administration sub profile corresponding to an extended bolus having an extended bolus volume B_extended, an algorithm may be performed according to the following pseudo-code

```
if B <= BT
    B_immediate = B
    B_extended = 0
else
    B_immediate = BT
    B_extended = B-BT,
``` where B is the bolus volume and BT is the bolus volume threshold BT.

In still further embodiments, a bolus volume of a bolus to be administered may be split into an immediate bolus and an extended bolus according to further algorithms such as those described herein or those known in the art.

In some cases, the administration of more than one bolus within a comparatively short period of times may be commanded such as, for example, by a patient. The second bolus administration may be commanded at a time when the depot is not empty but partly filled due to the first bolus. For example, a patient may administer a bolus before a meal and decide later that the administered bolus was inappropriately small. Similarly, a patient may recognize that the volume of an administered bolus was too small by mistake. In such cases, the first bolus may be considered for determining the bolus administration profile of the second bolus.

In embodiments of the present disclosure, the administration device may be adapted to administer a first bolus having a first bolus volume and a second bolus having a second bolus volume. The bolus administration profile controller 85 may be adapted to determine a first bolus administration profile and a further bolus administration profile such that if the administration of the first bolus is in progress when the administration of the second bolus is commanded, the further bolus administration profile is determined based, at least in part, on the first bolus administration profile and/or on the administration state of the first bolus.

For example, the first bolus may be taken into account by the bolus administration profile controller for determining the second bolus administration profile of the second bolus such that the depot volume of a depot does not exceed a depot volume threshold. The second bolus administration profile of the second bolus may be determined based, for example, on equation (3b) and take into account the partly filled depot when commanding the administration of the second bolus by the initial depot volume. The administration state of the first bolus is indicative of the portion of the first bolus volume that remains to be delivered when commanding the administration of the second bolus. The further administration profile may determine the second administration profile of the second bolus such that the bolus is continued to be administered according the first bolus administration profile. Alternatively, the further administration profile may determine the administration profile of the remaining portion of the first bolus as well as the administration profile of the second bolus. According to another embodiment, the administration of the second bolus is delayed until the administration of the first bolus is finished.

In further embodiments, the administration device is adapted to perform a basal administration according to a basal profile. The basal profile may be a patient-specific and time-of day-dependent basal profile, as graphically depicted in FIG. 2a. In the framework of diabetes therapy with the drug being insulin, the basal administration rate RB may, for example, vary between about 0.8 IU/h and about 2.0 IU/h over the day. In some embodiments, basal administration is performed by administering basal pulses. The basal pulses may either be administered with a constant basal pulse interval dt (FIG. 2b) between the basal pulses with the basal pulse volume being adjusted in accordance with the basal administration rate RB, or may have a constant basal pulse volume with the basal pulse interval dt being adjusted in accordance with the basal administration rate RB.

In embodiments of an administration device, the administration device is adapted to administer an extended bolus as a series of extended bolus pulses and perform a basal administration according to a basal profile. The controller unit may be adapted to control the administration unit to administer combined pulses, where each combined pulse comprises an extended bolus pulse and a basal pulse.

In one type of embodiment, the combined pulses are administered as consecutive pulses with no further basal pulses being administered between the combined pulses. In another type of embodiment, the combined pulses are administered as non-consecutive pulses with the administration of each combined pulse being followed by the administration of at least one basal pulse.

In further embodiments, the administration device is adapted to administer combined pulses, and the bolus administration profile controller is adapted to determine the bolus administration profile such that the combined pulse volume of the combined pulses does not exceed a pulse volume threshold.

Bolus administration profiles where the combined pulse volume does not exceed a given pulse volume may be employed when the basal pulse volume is not negligible as compared to the bolus pulse volume. The basal pulse amount can be determined by the basal profile and the basal administration profile. The bolus pulse volume can be adapted to meet the restriction for the combined pulse volume.

The pulse volume threshold may be computed based on a given depot volume threshold, for example, using the absorption model described herein.

The pulse volume threshold may be defined such that the depot volume of a depot does not exceed a maximum depot volume. Alternatively, the depot volume threshold may be defined to be smaller than the maximum depot volume, and to be a given fraction of the maximum depot volume in order to reduce the physical stress which is exerted onto the tissue. The fraction may be in the range from about 0.5 to about 0.8, for example.

In some embodiments, the administration device is adapted for administering drug pulses, and the bolus administration profile controller is adapted to determine the pulse volume and/or of the pulse interval such that the depot volume of a depot does not exceed a depot volume threshold.

The depot volume threshold may be defined such that the depot volume of a depot does not exceed a maximum depot volume. Alternatively, the depot volume threshold may be defined to be smaller than the maximum depot volume, and to be a given fraction of the maximum depot volume in order to reduce the physical stress which is exerted onto the tissue. The fraction may be in the range from about 0.5 to about 0.8, for example.

In further embodiments, the administration device comprises a user interface that is coupled to the controller unit and adapted to receive a bolus administration command. The user interface may comprise entry elements such as pushbutton, coordinate switches, a numeric keypad, or the like. Also, the user interface may comprise output elements such as, for example, a display. The display may be a Liquid Crystal Display (LCD) or an Organic Light Emitting Diode (OLED) display. The user interface may further comprise non-visual indicator elements, such as an acoustic indicator and/or a tactile indicator. In some embodiments, a housing comprises, at least in part, the user interface. In addition or alternative to the housing comprising the user interface, a remote user interface may be coupled to the controller unit via a wireless data interface. The remote user interface may be a fully functional user interface including entry and output elements, or may offer a reduced set of operational functions. A remote user interface offering a reduced set of operational functions may, for example, be comprised by a key fob like device and may only offer the entry of boli to be administered.

Dependent on the type of user interface, bolus administration commands may be received by the user interface in different ways. In some embodiments, a bolus volume may be entered in a bolus entry mode of the administration device using up and down buttons for increasing and decreasing the bolus volume, followed by a succeeding confirmation. Alternatively or additionally, a bolus may be entered by multiple keystrokes of a defined key, wherein each keystroke increases the bolus volume by a given increment.

In embodiments comprising a user interface adapted to receive a bolus administration command, the user interface may be adapted to indicate the reception of a bolus command with the administration device being, concealed from view. In further embodiments, the user interface is further adapted to indicate a received bolus volume with the administration device being, at least in part, concealed from view. Both indicating the reception of a bolus administration command and indicating the received bolus volume may be performed via an acoustic indicator and/or tactile indicator. The acoustic indicator and/or the tactile indicator may be controlled to emit a series of indication pulses, with each indication pulse being representative for a given bolus increment. In further embodiments, the bolus volume is displayed on a display being comprised by a remote user interface.

In some embodiments, the administration device controller is adapted to be selectively deactivated. The user interface may allow the manual selection of a bolus administration profile. The bolus administration profile controller can be deactivated if a bolus administration profile for a bolus to be administered is manually selected. Specifically, the selected bolus administration profile may be a member of a set of defined bolus administration profiles stored by the controller.

In embodiments comprising a bolus administration profile controller which is adapted to be selectively deactivated, the user interface may offer at least two different ways of receiving a bolus administration command and the bolus administration profile controller may be adapted to be selectively deactivated in dependence on the way the bolus administration command is received by the user interface. For example, the bolus administration profile controller may be deactivated if a bolus administration command is received by a first user interface which is integral with the administration device and offers direct input of a desired bolus administration profile. While, the bolus administration profile controller may be activated if a bolus administration command is received from a second user interface such as, for example, a key fob like remote user interface which offers only bolus volume input capabilities. Similarly, the bolus administration profile controller may be activated if a bolus administration command is received from a portion of the user interface which is integral with the administration device housing, offers a limited set of functions and is adapted to be operated with the administration device being concealed from view.

In embodiments allowing for selectively deactivating the bolus administration profile controller, the bolus administration profile controller may be deactivated by a user (e.g., a healthcare professional and/or a patient) by a user interface and/or a data interface of the administration device.

Methods for controlling a pump unit of an administration device are described herein. In one embodiment, the administration device is adapted for the subcutaneous administration of a liquid drug over an extended period of time. Referring to FIG. 4, the method may include: providing a bolus volume of a bolus to be administered; determining by a bolus administration profile controller 85 a bolus administration profile of the bolus to be administered, at least in part, based on the bolus volume, such that the depot volume of a depot is limited; and controlling the pump unit 60 to administer the bolus according to the bolus administration profile determined by the bolus administration profile controller 85.

The method may be carried out using administration devices as described herein.

The method may further comprise the step of providing a drug reservoir, the drug reservoir being filled with insulin such as, for example, for providing diabetes therapy via CSII.

In some embodiments, the method comprises the step of determining the bolus administration profile partly based on the pharmacokinetics of the insulin and/or on food absorption characteristics.

For different types of insulin having different pharmacokinetics, different bolus administration profiles may be appropriate. The pharmacokinetics may be taken into account in addition to the bolus volume determining the bolus administration profile. For example, for slow-acting insulin, a shorter period of time may be appropriate for the bolus administration as compared to a very short acting insulin analogue. Furthermore, different bolus administration profiles may be appropriate for different kinds of food. The food type may be taken into account in addition to the bolus volume for determining the bolus administration profile. For example, for a meal comprising considerable volumes of both fat and carbohydrates, such as pizza, a longer period of time may be appropriate for the bolus administration as compared to a meal comprising mainly carbohydrates, such as most fruits or Spaghetti. A food database may be provided for entering food absorption characteristics. A semi-quantitative selection option such as, for example, 'slow absorption', 'medium absorption' or 'fast absorption' may be provided. The entry of at least one numerical value characterizing the absorption characteristics may also be provided. Embodiments of the present disclosure may comprise a food database, semi-quantitative selection, numerical entry, or combinations thereof.

In further embodiments, the method comprises the step of determining the bolus volume based, at least in part, on a blood glucose value of a diabetic person. An insulin bolus may be administered in order to lower an undesirably high blood glucose value. Blood glucose values may be determined at specific points in time using commercially available blood glucose meters such as, for example, ACCU-CHECK® Compact plus or ACCU-CHECK® Aviva, both of which available from Roche Diagnostics. Blood glucose values may also be determined on a continuous or quasi-continuous basis by a continuous blood glucose monitor, as known in the art.

Based on the physiological characteristics and potential further input, such as carbohydrate intake, a bolus volume may be determined according to different methods known in the art. A variety of methods are known in the art for computing the bolus volume of an insulin bolus based on blood glucose measurements such as, but not limited to the disclosure in WO 2007/056592, which is incorporated by reference herein.

Collectively referring to FIGS. 3 and 4, where FIG. 3 schematically depicts an administration device according to the embodiments described herein and FIG. 4 schematically depicts an internal structure of such an administration device. Embodiments of the administration device may perform insulin administration in the framework of diabetes therapy using CSII and the present disclosure refers to diabetes therapy. However, the administration device may be used for other therapies such as, for example, pain therapy or cancer therapy with little or no modifications.

According to one embodiment, as depicted in FIG. 3, the administration device comprises a housing 10 enclosing the other device components. The housing 10 is adapted to be virtually continuously worn by a user (e.g., a patient) both night and day. While worn, the housing 10 may be concealed from view, i.e., without attracting attention. The housing 10 may be carried in a belt holster, in a trouser pocket, like a necklace, or the like.

According to another embodiment, the administration device comprises a drug reservoir 20, an infusion line 29 and an infusion line adapter 25 coupling the infusion line 29 to the drug reservoir 20. As depicted in FIG. 3, the housing 10, the drug reservoir 20 and the infusion line adapter 25 form a sealed and watertight unit in the assembled state. The infusion line 29 is connected to an infusion cannula (not visible in the figures). The infusion cannula may be placed in the subcutaneous tissue and replaced by the user every few days. The drug reservoir 20 may, for example, comprise 3.15 ml of insulin, with each ml of insulin corresponding to 100 International Units (IU) of insulin.

Further embodiments of the administration device comprise a user interface 50. The user interface 50 may comprise side face pushbuttons 42, 44, a menu pushbutton 46, a select pushbutton 48, a display 30, an acoustic indicator 33 (e.g., a buzzer) and a tactile indicator 35 (e.g., a pager vibrator). The display 30 may be a graphical Liquid Crystal Display (LCD) used to provide multiple kinds of information such as, for example, operation mode information, time, date, bolus information, alerts, error messages, current basal infusion rate information, menu items for programming the administration device, and the like. The acoustic indicator 33 and the tactile indicator 35 are provided for providing non-visual user such as, for example, warning and alarming purposes. Additionally, it is noted that the acoustic indicator 33 and the tactile indicator 35 may provide non-visual user feedback on user operations if the display 30 is not comfortable and discretely accessible because the administration device is, for example, carried under the cloths.

Still referring to FIG. 3, the side face pushbuttons 42, 44, the menu pushbutton 46, and the select pushbutton 48 are provided for operational purposes. In one embodiment the menu pushbutton 46 and the select pushbutton 48 are arranged on the front face of the housing 10. The menu pushbutton 46 is used to access different data entry and programming menus. The select pushbutton is used to accept and confirm entries. Side face pushbuttons 42, 44 are arranged at a side face of the housing 10 next to the infusion line adapter 25. The side face pushbuttons 42, 44 are designed to be easily and securely operated even if they are not visible. Thus, the side face pushbuttons 42, 44 may be operated through a layer of cloths, or the like. In one embodiment, the side face pushbuttons 42, 44 project with respect to the housing 10 to be easily sensed and provide tactile force feedback when being operated. The side face pushbuttons 42, 44 can be used for selecting items from a menu, for increasing/decreasing numeric values during entry and for commanding the administration of boli as is described in more detail below.

A pump unit 60 and a supervision unit 63 may be provided for performing the drug administration. In one embodiment, the pump unit 60 comprises a motor-driven spindle drive and the supervision unit 63 comprises a force sensor and a rotary encoder. In combination, the drug reservoir 20, the pump unit 60 and the supervision unit 63 form the administration unit 70. Several suitable designs for the administration unit 70 and the pump unit 60 are known in art and may be designed, for example according to the disclosures of EP1124600B1 or EP0991440B1, which are incorporated by reference herein.

The operation of the administration device is controlled by the controller unit 80. The Controller unit 80 may comprise an electronics circuit and all the elements typical of control circuits of similar administration devices such as, for example, one or multiple micro controllers, static memory, dynamic memory, clock circuitry, a power circuit for controlling the pump unit 60, safety circuits, and the like. Additionally, the controller unit 80 may be connected to a power supply such as a rechargeable or non-rechargeable battery.

For a pump unit comprising a motor-driven spindle drive, administration can be controlled by controlling the motor shaft rotation. Fractional rotation of the motor shaft may be performed for the administration of small pulses. Multiple rotations of the rotary shaft may be performed for the administration of a larger drug volume. During the administration of larger drug volumes with virtually continuous operation of the rotary motor of the pump unit 60, the administration rate may typically be performed with a substantially steady administration rate and a flow of, e.g., about 0.25 IU/sec. During the administration of small drug volumes, typically no steady state is reached and the flow at the cannula is pulse-like. Pulsed drug administration is modeled and described with reference to a Dirac pulse of negligible duration. However, it is noted that Dirac pulses are described herein for clarity without requiring the embodiments described herein to be bound to any particular theory.

Referring again to FIG. 4, embodiments of the administration device further comprise two bidirectional data interfaces, namely an Infra Red (IR) data interface 90 and a Radio Frequency (RF) data interface 95, according, for example, to the BLUETOOTH standard. The IR data interface 90 may exchange data with virtually every external standard device (e.g., a PC or a Personal Digital Assistant PDA). The IR data interface 90 may be used, e.g., for downloading history data to an external device or for uploading configuration data to the administration device. The RF data interface 95 may be used, e.g., for transferring remotely generated administration commands to the administration device and for further remote control purposes. Either or both of the IR data interface 90 and the RF data interface 95 may be adapted to receive a bolus volume.

The administration device may be operated in an administration mode or a suspend mode. The administration device is operated in the suspend mode when no drug is to be administered. The suspend mode may be chosen, for example, for replacing the drug reservoir 20, when temporarily removing the administration device (e.g., during sportive activities), or for changing configuration parameters of the administration device. The administration device may further change from the administration mode into the suspend mode autonomously such as in the case of an administration device failure, for example.

The administration device may also be operated in the administration mode. In the administration mode, the administration device is adapted for drug administration according to two administration regimes that are overlaid and carried out simultaneously.

The first of the two administration regimes is a basal administration regime. According to the basal administration regime, the controller unit 80 controls the pump unit 60 to administer drug according to a basal profile. In the framework of diabetes therapy, the basal administration covers the patient's basal, i.e., meal independent, insulin demand for maintaining the patient's metabolism. In this framework, the basal profile typically shows a 24 hour cycle with the administration rate being substantially constant within each hour of a day and being generally different for different hours of the day. The basal profile may be configured either using the user interface 50 of the administration device, via the IR data interface 90 or via the RF data interface 95.

Figure 5:
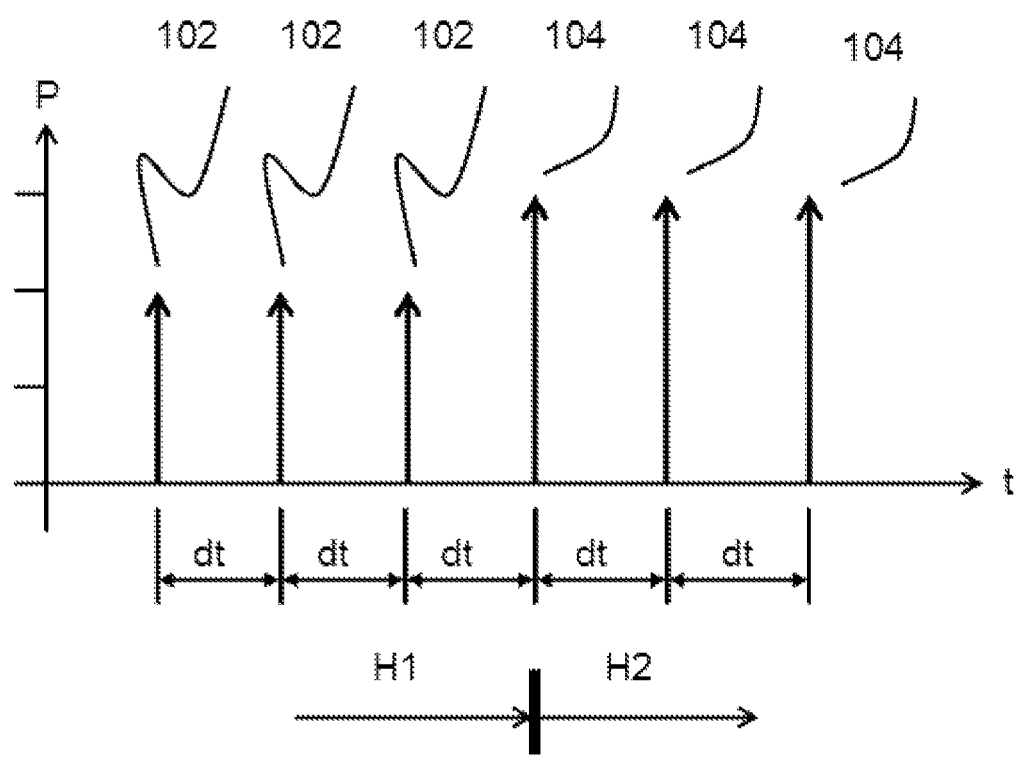
FIG. 5 depicts a basal administration profile for basal administration according to one or more of the embodiments shown and described herein.

Referring now to FIG. 5, a basal administration profile comprising a quasi-continuous administration of relatively small basal pulses administered with a fixed basal pulse interval dt is graphically depicted. The fixed basal pulse interval dt may, e.g., be about 3 minutes. Correspondingly, the basal pulse volume is about 1/20 of the total hourly basal drug volume. Basal pulses 102 are administered at fixed points in time. For example, with the basal pulse interval dt being about 3 minutes, a basal pulse 102 is administered every full hour, 3 minutes after the full hour, 6 minutes after the full hour and so on. In similar embodiments, the basal pulses may be administered at different points of time and/or with a different basal pulse interval dt of, e.g., about 6 minutes or about 15 minutes.

Basal pulses 102 belong to a first hour of day H1, while basal pulses 104 belong to a second hour of day H2. As depicted in FIG. 5, the administration rate of the second hour of day H2 is about 1.5 times the administration rate of the first hour of day H1. For example, the administration rate in the first hour of day H1 may be about 0.8 IU/hr and the administration rate of the second hour of day H2 may be about 1.2 IU/hr.

The second administration regime is a bolus administration regime. In the framework of diabetes therapy, the administration of insulin boli may cover the intake of carbohydrates in order to lower undesirably high blood glucose values. While spreading bolus administration over an extended period of time may be desirable for pharmacokinetic reasons in some cases, it may be desirable to perform bolus administration within a short period of time. Bolus administration according to the second administration regime may be performed at any point in time while continuing the basal administration according to the first administration regime.

Referring again to FIGS. 3 and 4, options are provided herein for commanding the administration of a bolus. According to a first method for commanding the administration of a bolus, a standard bolus administration menu may be activated using the menu pushbutton 46 and the select pushbutton 48. In the standard bolus administration menu, a bolus volume to be administered may be increased and decreased via the side face pushbuttons 42, 44. For example, the bolus volume may be shown on the display 30 while the bolus volume is being entered. After finishing the entry, the entry may be confirmed by pressing the select pushbutton 48. This method of commanding the administration of a bolus utilizes the side face pushbuttons 42, 44, the menu pushbutton 46, the select pushbutton 48, and the display 30.

A second method for commanding the administration of a bolus only utilizes the side face pushbuttons 42, 44 and does not require the display 30 to be visible. According to this method, one of the side face pushbuttons 42, 44 is continuously activated for a time of, e.g., about 3 seconds in order to commence a blind bolus entry mode. Once the blind bolus entry mode is commenced, the bolus volume to be administered may be entered by operating the other of the two side face pushbuttons 42, 44 consecutively a number of times to increase or decrease the bolus volume. For example, the bolus volume to be administered may be increased with each keystroke by a given bolus increment of, e.g., about 0.5 IU. Acoustic and/or tactile feedback may also be provided to confirm correct entry of the bolus volume.

Prior to controlling the pump unit 60 to administer the bolus, an appropriate bolus administration profile may be determined by the bolus administration profile controller 85. According to the embodiments described herein, drug absorption may be considered following the empirical model. However, further physical absorption models may be used in alternative embodiments of the bolus administration profile controller 85.

Figure 6:
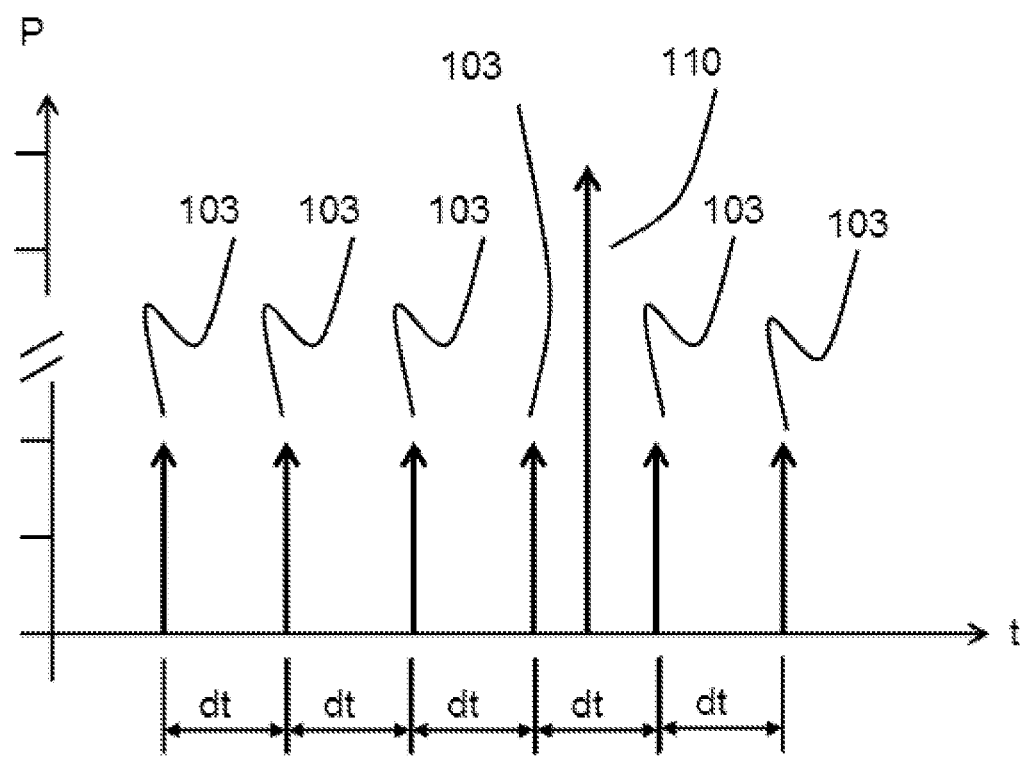
FIG. 6 depicts an administration profile comprising basal administration and bolus administration with the bolus volume being below a bolus volume threshold according to one or more of the embodiments shown and described herein.

FIG. 6 graphically depicts an administration profile comprising a basal administration profile with basal pulses 103 and an immediate bolus pulse 110. Referring collectively to FIGS. 3, 4 and 6, in one embodiment, if the bolus volume of a bolus to be administered is below a given bolus volume threshold, the bolus administration profile controller 85 adjusts the bolus administration profile to include an immediate bolus pulse 110. The bolus volume threshold is stored in a memory of the controller unit 80 and may be altered via the user interface 50, via the IR data interface 90 or via the RF data interface 95 (e.g., by the patient and/or a healthcare professional). The administration of an immediate bolus may result in the bolus volume being temporarily stored in a depot with delayed administration from the depot.

The bolus volume threshold is typically configured to be in the range of some International Units. For example, the bolus volume threshold may equal to about 7.0 IU for a steel infusion cannula set into the tissue transverse to the skin with a steady state flow of about 0.25 IU/sec. As a rule of thumb, the bolus volume threshold in IU's is about equal to the cannula length in mm for a steel cannula which is transversally set into the skin. More generally, the bolus value threshold may be configured such that the bolus depot volume resulting from the bolus administration does not exceed a given depot volume threshold and does not exceed a maximum depot volume.

If the bolus volume to be administered exceeds the bolus volume threshold BT, the bolus administration profile controller 85 may determine a bolus administration profile with the bolus volume being split into a first bolus sub volume and a second bolus sub volume. The first bolus sub volume is administered according to a first bolus administration sub profile while the second bolus sub volume is administered according to a second bolus administration sub profile. The first bolus administration sub profile is an immediate bolus administration profile while the second bolus administration sub profile is an extended bolus administration profile, resulting in the first bolus sub volume being an immediate bolus volume B_immediate and the second bolus sub volume being an extend bolus volume B_extended given by $$B\_extended = B - B\_immediate, \quad (6)$$

where B is the bolus volume.

Figure 7:
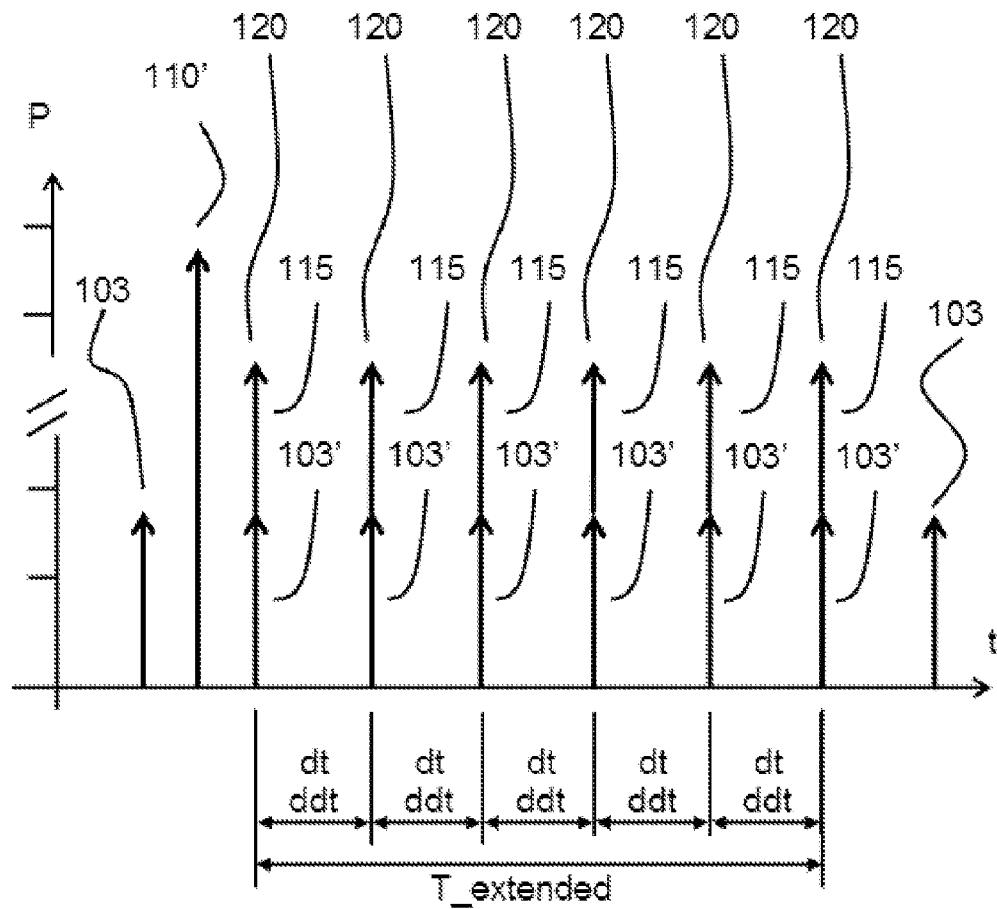
FIG. 7 depicts an administration profile comprising basal administration and bolus administration with the bolus volume being above a bolus volume threshold according to one or more of the embodiments shown and described herein.

Referring now to FIG. 7, a bolus administration profile is depicted. In one embodiment, the immediate bolus volume B_immediate is made equal the bolus volume threshold BT and is administered as immediate bolus pulse 110'. The extended bolus volume B_extended is divided into a number of extended bolus pulses 115 with each individual extended bolus pulse 115 having an identical bolus pulse volume. The extended bolus pulses 115 are administered along with a series of consecutive basal pulses 103'. The resulting in combined pluses 120 (depicted in FIG. 7 as stacked arrows) are administered at fixed points in time with each combined pulse 120 comprising an extended bolus pulse 115 and a basal pulse 103'. The combined pulses have a bolus pulse interval ddt equal to the basal pulse interval dt. The basal pulses 103' of the combined pulses 120 are determined by the basal administration profile and have the same basal pulse volume as the basal pulses 103. The extended period of time T_extended may be set by the user (e.g., patient and/or a healthcare professional) as a configuration parameter. The configuration parameter may have a value of, e.g., about 15 minutes or 30 minutes. In some embodiments, the extended period of time T_extended is a multiple of the bolus pulse interval ddt. In other embodiments, at least two different extended periods of time are provided as configuration parameters. The extended period of time T_extended for administering the extended bolus may be selected among the provided time periods in dependence on the extended bolus volume B_extended. For example, the extended period of time T_extended may be determined such that the bolus depot volume resulting from the bolus administration does not exceed a maximum depot volume threshold and does not exceed a maximum depot volume.

In many cases, the combined pulse volume of the combined pulses 120 is sufficiently small and the bolus pulse interval ddt is sufficiently large to ensure absorption of a combined pulse 120 in the interval ddt if the extended period of time is set to a fixed value of, e.g., about 30 minutes.

The bolus pulse volume P_bolus of each extended bolus pulse 115 may be computed for a uniform distribution of the extended bolus volume onto all combined pulses 120 by $$P\_bolus = B\_extended/(T\_extended/ddt+1), \quad (7)$$

where B_extended is the extended bolus volume, T_extended is the extended period of time, and ddt is the bolus pulse interval. The denominator of equation (7) equals the number of combined pulses. Each of the extended bolus pulses 115 may be administered along with the each basal pulse 103' after the administration of the bolus is commanded.

In further embodiments, the immediate bolus may be administered after administering the extended bolus or the immediate bolus may be administered while administering the extended bolus.

It may be desired to manually determine the bolus administration profile independent of the bolus administration profile controller 85. For example, the bolus administration profile may take into account the glycemic response of special food types of complex glycemic characteristics and slow carbohydrate absorption, such as menu dinner. For special food types the bolus administration over an extended period of time T_extended may be appropriate even for a bolus volume below the bolus volume threshold BT. Accordingly, dedicated bolus administration profiles may be manually selected via the user interface 50. In other embodiments, the bolus administration profile controller 85 determines the bolus administration profile taking into account both bolus volume and glycemic food characteristics.

Referring again to FIGS. 3 and 4, the controller unit 80 may further be configured to activate the bolus administration profile controller 85 only if the side face pushbuttons 42, 44 and/or either of the IR data interface 90 or the RF data interface 95 are used for commanding the bolus administration and entering the bolus volume. The controller unit 80 may also deactivate the bolus administration profile controller 85 if the menu pushbutton 46 and the select pushbutton 48 are used. Therefore, a bolus administration may be commanded via the side face push buttons 42, 44 without access to all elements of the user interface. Furthermore, while a bolus administration profile which is appropriate in most cases may be automatically selected, the user may also have full manual control over the bolus administration profile when desired.

The controller unit 80 may further be configured to generally deactivate the bolus administration profile controller 85.

Figure 8:
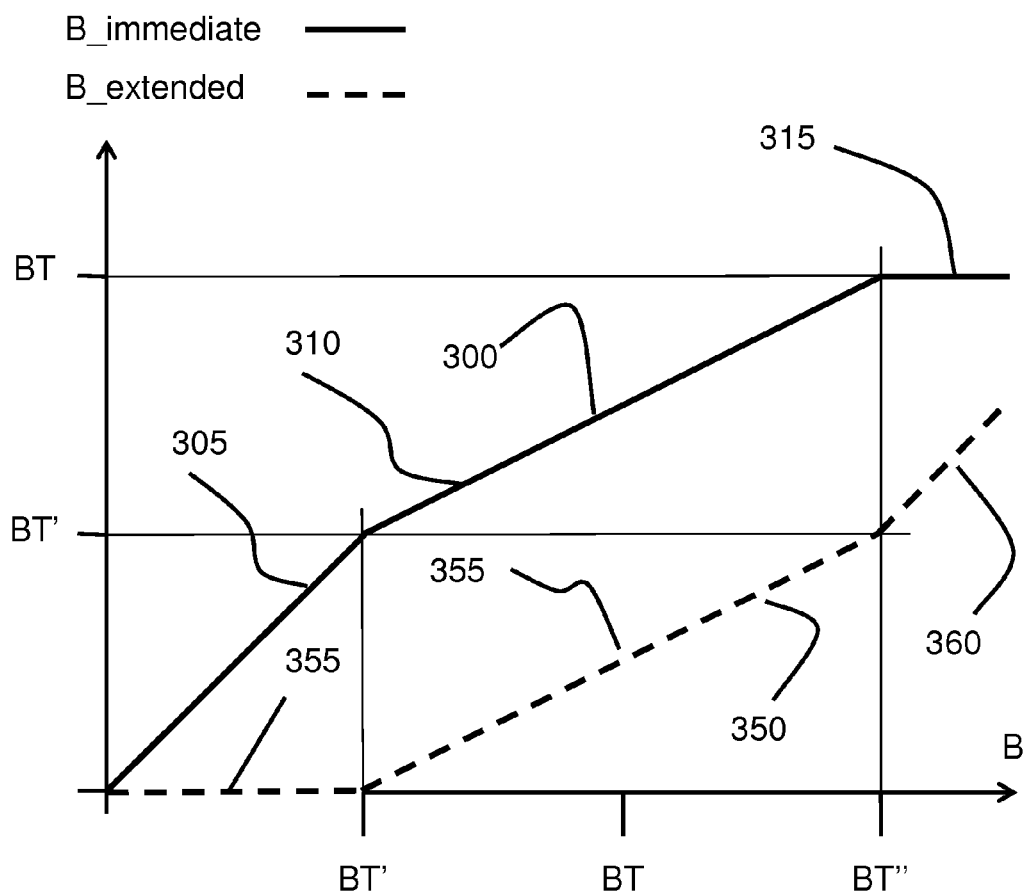
FIG. 8 depicts a splitting of a bolus into an immediate bolus and an extended bolus according to one or more of the embodiments shown and described herein.

Referring now to FIG. 8, the splitting of a bolus volume into an immediate bolus volume B_immediate and an extended bolus volume B_extended is graphically depicted. In one embodiment, the bolus volume is split into an immediate bolus volume B_immediate and an extended bolus volume B_extended for a bolus volume exceeding a bolus splitting threshold BT'. The bolus splitting threshold BT' is generally smaller than the bolus volume threshold BT. As seen from the solid line 300 representing the immediate bolus volume B_immediate, the immediate bolus volume B_immediate equals the bolus volume while the bolus volume is smaller than the bolus splitting threshold BT' and the extended bolus volume B_extended represented by the dashed line 355 is zero while the bolus volume is smaller than the bolus splitting threshold BT'. For a bolus volume exceeding the bolus splitting threshold BT', the portion of the bolus volume which exceeds the bolus splitting threshold BT' is split into equal parts. Each part increases to the immediate bolus volume B_immediate and an extended bolus volume B_extended, as shown by the segments 310, 350 of equal slopes. The splitting of the bolus graphically depicted in FIG. 8 can be calculated by $$B' = B - BT', \quad (8)$$

$$B\_immediate = BT' + B'/2, \text{ and} \quad (9)$$

$$B\_extended = B'/2, \quad (10)$$

where B' is the portion of the bolus volume which exceeds the bolus splitting threshold, B is the bolus volume, BT' is the bolus splitting threshold, B_immediate is the immediate bolus volume and B_extended is the extended bolus volume.

While the bolus splitting threshold BT' is depicted as half the bolus volume threshold BT, it is noted that bolus splitting threshold BT' may be any percentage of the bolus volume threshold BT.

A limiting bolus volume threshold BT'' is defined as the bolus volume B for which the immediate bolus volume B_immediate equals the bolus volume threshold BT. As may be seen from the segment 315 the immediate bolus volume B_immediate does not increase beyond the limiting bolus volume threshold BT'' for an increasing bolus volume B. While as depicted by segment 360, the bolus volume B exceeding the limiting bolus volume threshold BT'' increased the extended bolus volume B_extended. As depicted in FIG. 8, the limiting bolus volume threshold BT'' equals 3/2*BT. For the bolus volume B exceeding the limiting bolus volume threshold BT'' the bolus may be administered as uniform distribution such as, for example, according to equation (7).

The transition between the administration of an immediate bolus only and the administration of both an immediate bolus and an extended bolus is may be smoothed according to the embodiments described herein. It is noted those skilled in the art may readily vary the threshold values and the splitting algorithms to achieve smoothing without departing from the scope of the present disclosure. Furthermore, it is noted that the bolus administration profile controller 85 (FIG. 4) may directly compute the immediate bolus volume B_immediate and the extended bolus volume B_extended according to an equation or may employ a look-up table.

Figure 9:
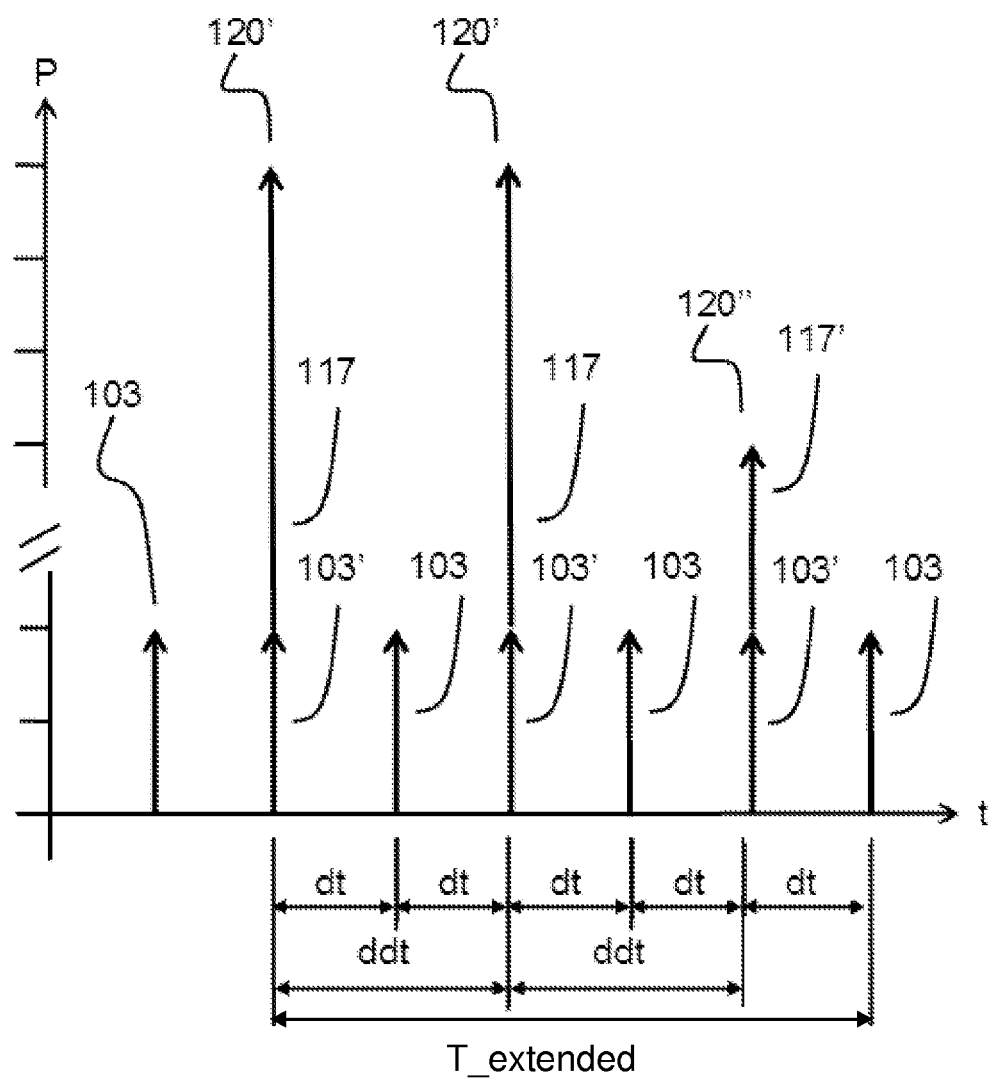
FIG. 9 depicts an administration profile comprising basal administration and bolus administration with the bolus volume being above a bolus volume threshold according to according to one or more of the embodiments shown and described herein.

Referring now to FIG. 9, the administration of a bolus exceeding the bolus volume threshold BT is graphically depicted. In one embodiment, the bolus administration profile controller 85 determines a bolus administration profile such that the bolus is split into a number of extended bolus pulses 117, 117' which are administered along with a series of non-consecutive basal pulses 103'. This bolus administration profile results in the administration of a sequence of a combined pulses 120', 120" where each combined pulse 120' is followed by at least one basal pulse 103. For example as depicted in FIG. 9, each combined pulse 120' is followed by one basal pulse 103, which results in the bolus pulse interval ddt being double the basal pulse interval dt. The extended bolus pulse volume of the extended bolus pulses 117 equals a bolus pulse volume threshold. The number n_bolus of extended bolus pulses 117, 117' is given by $$n\_bolus = \mathrm{ceil}(B/PT\_bolus), \quad (11)$$

where 'cell' indicates integral rounding up, B is the bolus volume and, PT_bolus is the bolus pulse volume threshold. Since the bolus volume is generally not an integral multiple of the bolus pulse volume threshold, the last extended bolus pulse 117' is typically smaller than the preceding extended bolus pulses 117. Thus, the volume of the last combined pulse 120" is accordingly smaller than of the preceding combined pulses 120'. In a further embodiment, the bolus administration profile controller 85 determines the bolus administration profile such that the extended bolus pulse volume is equal for all extended bolus pulses 117, 117'.

Specifically, the bolus pulse volume threshold may be determined such that it is absorbed by delayed absorption in a time period equal to the bolus pulse interval ddt given by $$ddt = 2*dt, \quad (12)$$

where dt is the basal pulse interval. Additionally, the basal pulse volume of the basal pulses 103 may be small enough not to be considered with respect to absorption.

It will be apparent to those skilled in the art that various modifications and variations can be made to the embodiments described herein without departing from the spirit and the scope of the claimed subject matter. Thus it is intended that the specification cover the modifications and variations of the various embodiments described herein provided such modifications and variations come within the scope of the appended claims and their equivalents.

What is claimed is:

1. An administration device for subcutaneous administration of a liquid drug to tissue of a patient over an extended period of time, the administration device comprising:
   an administration unit, the administration unit comprising a drug reservoir and a pump unit;
   a housing, the housing comprising the administration unit and being adapted to be carried by a patient over an extended period of time;
   a cannula; and
   a controller unit, the controller unit comprising a bolus administration profile controller, wherein: the bolus administration profile controller receives a bolus volume of a bolus to be administered; and determines based, at least in part, on the received bolus volume a bolus administration profile such that a depot volume of a depot is limited, said depot being a locally concentrated drug cloud in the subcutaneous tissue around the cannula, wherein the depot is a subcutaneous drug depot that is present during and shortly after the administration until the drug is absorbed by the tissue;
   wherein the administration device is configured for the subcutaneous administration of the liquid drug; and
   wherein the controller unit is configured to implement a code for the bolus administration based on an absorption model for the subcutaneous administration to determine a resulting depot volume of the bolus by accounting for a steady absorption bolus volume, a maximum steady absorption rate, and an administration time when the depot is empty at the beginning of the administration and when the depot is not empty, as a function of a time of zero at a beginning of administration to an administration time;
   wherein the steady absorption bolus volume of the absorption model is given by:

$$B\_steady = R\_max \cdot T\_admin$$

wherein B_steady is the steady absorption bolus volume, R_max is the maximum steady absorption rate, and T_admin is the administration time;
   wherein if the depot is empty at the beginning of the administration the resulting depot volume of the bolus while performing the administration is given as a function of time by:

$$B\_depot(t1) = \int_0^{t1} [F(\tau) - R\_max] d\tau$$

wherein B_depot is the depot volume, F is the actual flow, R_max is the maximum steady absorption rate, T_admin is the administration time and t1 runs from zero at the beginning of the administration to the administration time; and
   wherein if the depot is not empty at the beginning of the administration, the resulting depot volume is given by:

$$B\_depot(t1) = \int_0^{t1} [F(\tau) - R\_max] d\tau + B0\_depot$$

wherein B0_depot is the initial depot volume.

2. The administration device of claim 1 further comprising a user interface, wherein the user interface is coupled to the controller unit and receives a bolus administration command.

3. The administration device of claim 2 wherein the user interface indicates a reception of the bolus administration command with the administration device being concealed from view.

4. The administration device of claim 1 wherein the bolus administration profile controller is adapted to be selectively deactivated.

5. The administration device of claim 4 wherein a user interface receives a bolus administration command in at least two different ways and the bolus administration profile controller is selectively deactivated in dependence upon the at least two different ways the bolus administration command is received by the user interface.

6. The administration device of claim 1 wherein the depot volume of the depot does not exceed a depot volume threshold.

7. The administration device of claim 6 wherein the depot volume threshold is defined to be smaller than a maximum depot volume, and to be a fraction of the maximum depot volume between about 0.5 to about 0.8 in order to reduce a physical stress exerted onto the tissue.

8. The administration device of claim 1 wherein the bolus administration profile comprises an immediate bolus administration profile corresponding to an immediate bolus having an immediate bolus volume.

9. The administration device of claim 8 wherein the immediate bolus volume does not exceed a bolus volume threshold.

10. The administration device of claim 1 wherein the bolus administration profile comprises an extended bolus administration profile corresponding to an extended bolus having an extended bolus volume.

11. The administration device of claim 10 wherein the extended bolus is a series of extended bolus pulses.

12. The administration device of claim 11 wherein a bolus pulse volume of the extended bolus pulses does not exceed a bolus pulse volume threshold.

13. The administration device of claim 11 wherein the administration device performs a basal administration according to a basal profile.

14. The administration device of claim 13 wherein: the controller unit controls the administration unit; the administration unit administers combined pulses; and each of the combined pulses comprises an extended bolus pulse and a basal pulse.

15. The administration device of claim 14 wherein a combined pulse volume of the combined pulses does not exceed a pulse volume threshold.

16. The administration device of claim 1 wherein: the bolus administration profile comprises at least two bolus sub volumes; the at least two bolus sub volumes sum up to the bolus volume B; and the bolus administration profile controller determines the at least two bolus sub volumes.

17. The administration device of claim 1 wherein: the administration device administers drug pulses; the bolus administration profile controller determines a pulse volume and/or a pulse interval such that the depot volume of the depot does not exceed a depot volume threshold.

18. The administration device of claim 1 wherein the administration device administers a first bolus having a first bolus volume and a second bolus having a second bolus volume wherein the bolus administration profile controller determines a first administration profile and a further administration profile based at least in part on the first bolus administration profile and/or on an administration state of the first bolus when an administration of the second bolus is commanded while the second bolus is being administered.

19. A method for controlling a pump unit of an administration device, the administration device being adapted for subcutaneous administration of a liquid drug to tissue of a patient over an extended period of time, the method comprising:

providing a bolus volume of a bolus to be administered;
providing a controller unit, the controller unit comprising a bolus administration profile controller and wherein the controller unit is configured to implement a code for the bolus administration based on an absorption model for the subcutaneous administration to determine a resulting depot volume of the bolus by accounting for a steady absorption bolus volume, a maximum steady absorption rate, and an administration time when a depot is empty at the beginning of the administration and when the depot is not empty, as a function of a time of zero at a beginning of administration to an administration time;

wherein the steady absorption bolus volume of the absorption model is given by:

$$B\_steady = R\_max \cdot T\_admin$$

wherein B_steady is the steady absorption bolus volume, R_max is the maximum steady absorption rate, and T_admin is the administration time;

wherein if the depot is empty at the beginning of the administration the resulting depot volume of the bolus while performing the administration is given as a function of time by:

$$B\_depot(t1) = \int_0^{t1} [F(\tau) - R\_max]d\tau$$

wherein B_depot is the depot volume, F is the actual flow, R_max is the maximum steady absorption rate, T_admin is the administration time and t1 runs from zero at the beginning of the administration to the administration time; and wherein if the depot is not empty at the beginning of the administration, the resulting depot volume is given by:

$$B\_depot(t1) = \int_0^{t1} [F(\tau) - R\_max]d\tau + B0\_depot$$

wherein B0_depot is the initial depot volume;

determining, with the bolus administration profile controller, a bolus administration profile of the bolus to be administered, at least in part, based on the provided bolus volume, wherein the depot volume of the depot is limited, said depot being a locally concentrated drug cloud in the tissue around a cannula, and wherein the depot is a subcutaneous drug depot that is present during and shortly after the administration until the drug is absorbed by the tissue;

controlling the pump unit to administer the bolus according to the bolus administration profile determined by the bolus administration profile controller; and administering the liquid drug subcutaneously.

20. The method of claim 19 further comprising providing a drug reservoir comprising insulin.

21. The method of claim 20 further comprising determining the bolus administration profile based at least in part on pharmacokinetics of the insulin and/or on food absorption characteristics.

22. The method of claim 20 further comprising determining the bolus volume based at least in part on a blood glucose value of a diabetic person.

* * * * *

UNITED STATES PATENT AND TRADEMARK OFFICE
CERTIFICATE OF CORRECTION

PATENT NO.        : 8,715,268 B2
APPLICATION NO.   : 12/858480
DATED             : May 6, 2014
INVENTOR(S)       : Axel Remde et al.

It is certified that error appears in the above-identified patent and that said Letters Patent is hereby corrected as shown below:

In the Specification

Col. No. 3, Line No. 3-4, "threshold according to according to one or more" should read --threshold according to one or more--;

Col. No. 19, Line 7-9, "The resulting in combined pluses 120" should read --The resulting in combined pulses 120--;

Col. No. 20, Line 65, "bolus is may be smoothed" should read --bolus may be smoothed--.

Signed and Sealed this
Thirteenth Day of January, 2015

Michelle K. Lee
*Deputy Director of the United States Patent and Trademark Office*